United States Patent [19]
Schlatzer, Jr.

[11] 3,940,351
[45] Feb. 24, 1976

[54] POLYMERIZATION OF CARBOXYLIC ACID MONOMERS AND ALKYL ACRYLATE ESTERS IN CHLOROFLUOROETHANE

[75] Inventor: Robert K. Schlatzer, Jr., Chagrin Falls, Ohio

[73] Assignee: The B. F. Goodrich Company, Akron, Ohio

[22] Filed: Mar. 11, 1975

[21] Appl. No.: 557,295

Related U.S. Application Data

[63] Continuation-in-part of Ser. No. 485,125, July 2, 1974.

[52] U.S. Cl. 260/17.4 SG; 260/78.5 R; 260/78.5 T; 260/86.1 R; 260/89.5 R
[51] Int. Cl.² .............................................. C08L 5/00
[58] Field of Search... 260/17.45 G, 86.1 R, 89.5 R, 260/78.5 T, 80.3 R, 80.81

[56] References Cited
UNITED STATES PATENTS

| | | | |
|---|---|---|---|
| 2,798,053 | 7/1957 | Brown | 260/2.2 |
| 3,427,382 | 2/1969 | Haefele | 424/71 |
| 3,677,991 | 7/1972 | Moore | 260/29.6 |
| 3,788,995 | 1/1974 | Stahly | 260/86.1 |

OTHER PUBLICATIONS

Chem. Abs. 67:121,566 "Aqueous Colloidal Dispersion of Acrylic Polymers," Dupont.

*Primary Examiner*—Donald E. Czaja
*Assistant Examiner*—Edward Woodberry
*Attorney, Agent, or Firm*—J. Hughes Powell, Jr.

[57] ABSTRACT

Improved copolymers of unsaturated copolymerizable carboxylic acid monomers and one or more alkyl acrylate esters containing 10 to 30 carbon atoms which serve as efficient thickeners of aqueous solutions, even in the presence of substantial amounts of inorganic salts such as sodium chloride are prepared by conducting the polymerization of the comonomers in a chlorofluoroethane.

10 Claims, No Drawings

POLYMERIZATION OF CARBOXYLIC ACID MONOMERS AND ALKYL ACRYLATE ESTERS IN CHLOROFLUOROETHANE

CROSS REFERENCE TO RELATED APPLICATION

This is a continuation-in-part of my copending application Ser. No. 485,125 filed July 2, 1974.

BACKGROUND OF THE INVENTION

It is known (U.S. Pat. No. 2,798,053) that copolymers of carboxylic monomer such as acrylic acid and about 0.1 to 1.0 by weight of a polyalkenyl polyether crosslinker such as polyallyl sucrose are gel-like polymers which are insoluble in water and organic solvents and which, especially in the form of their salts, absorb large quantities of water or solvent with consequent many times increase in volume. Additional monomers taught by the patent as compatible with 40 to 95% by weight acrylic acid and 0.2 to 2.5% by weight polyalkenyl polyether are 4to 59% by weight methyl acrylate and 2-ethylhexyl acrylate. These polyelectrolyte polymers are useful as bodying and suspending agents in various mucilaginous and colloidal gel-like applications such as dentifrices, surgical jellies, creams and ointments, printing paste thickeners, and the like. A still unsolved problem is that most polyelectrolyte solutions decrease drastically in viscosity upon the addition of electrolytes such as sodium chloride. The prior art thickener materials are ion-sensitive and do not serve to efficiently maintain or increase the viscosities of water or organic solvent solutions containing inorganic salts such as sodium chloride even when a third monomer such as 2-ethylhexyl acrylate is included in the polymer as is suggested by the prior art patent. This property would be of great value, for instance, in thickening certain latexes, oil well drilling muds, food preparations, ionic detergents, dye pastes, cosmetic preparations, and pharmaceuticals. In some cases the problem is to thicken a solution containing a given amount of salt, as in a particular pharmaceutical recipe. In other cases it may be desired to maintain a constant viscosity level in a solution in which the amount of salt present is increasing, for example, in an automobile storage battery. My present application discloses useful copolymers of carboxylic acid polymers with acrylic esters containing 10 to 30 carbon atoms. Further improvement in these polymers and the process for making them is desired.

SUMMARY OF THE INVENTION

Improved copolymers of unsaturated copolymerizable carboxylic acid monomers with at least one acrylic ester containing about 10 to 30 carbon atoms are found to be more efficient water thickeners, which when neutralized by basic materials form water mucilages that have especially improved resistance to decrease in viscosity when salts are added thereto when such polymerization is conducted in the presence of a chlorofluoroethane, as compared to such materials polymerized in the prior art diluents or solvents. The polymers prepared in accordance with this invention not only are more efficient thickening agents than those prepared with other prior art solvents, but in many cases have more desirable consistency. Other advantages are that filterable slurries are obtained whereby the polymers are readily separated from the diluent, and certain copolymers which are not practically prepared in solvents such as benzene are readily prepared in accordance with this invention.

DETAILED DESCRIPTION OF THE INVENTION

Polymers of a carboxylic acid monomer and one or more acrylic esters having aliphatic chain length of 10 to 30 carbon atoms are found to be efficient water thickeners which, when neutralized by a basic material, form water mucilages that have much greater resistance to dropping sharply in viscosity when a salt such as sodium chloride is either added thereto, or is already present in said water system, than do the mucilages prepared with thickening agents known in the prior art. Depending on the proportion of the critical long chain aliphatic acrylates utilized, the polymers vary considerably in properties. Varying the proportion of the acrylate monomer serves to provide control of aqueous solution viscosity of the copolymer solutions, control of the rheology or flow properties of combinations of polymer and a solvent such as water, and to provide the ability to thicken ion containing water solutions with an efficiency heretofore not possible with prior art thickening agents.

The new copolymers provided by this invention may optionally be crosslinked by the inclusion in the polymer system of a crosslinking monomer selected from polymerizable compounds containing a polymerizable $CH_2=C<$ grouping and at least one other polymerizable grouping, the unsaturated bonds of said polymerizable grouping being nonconjugated with respect to each other.

When an optional crosslinking monomer is present, it serves to provide particular control of the rheology of the mucilage. With no crosslinker present, thickening agents containing less than 20–30 weight percent of acrylate ester often form solutions which are stringy in nature before a salt is added, but which become desirably smooth and buttery in appearance after the addition of salt. A solution or mucilage of a crosslinked thickener of this invention containing a suitable level of long chain alkyl acrylate or methacrylate is usually buttery in its initial appearance and maintains more constant solution viscosity in cases where salt is added to the solution in increasing amounts than do the prior art materials.

Highly useful carboxylic polymers are obtained when a carboxylic monomer such as acrylic acid, maleic acid or maleic anhydride, and the like is copolymerized with certain proportions of acrylic esters having long chain (from 10 to 30 carbon atoms) aliphatic groups and, optionally, with a crosslinking agent comprising a polymerizable compound containing a polymerizable $CH_2=C<$ grouping and at least one other polymerizable grouping, said groups being nonconjugated with respect to each other. These crosslinkers are typified by allyl acrylate, methallyl methacrylate, diallyl malonate, divinyl ether, glycol diacrylate (ethylene diacrylate), glyceryl triacrylate, and divinyl benzene.

A useful crosslinking material is a polyalkenyl polyether of a polyhydric alcohol containing more than one alkenyl ether grouping per molecule, the parent polyhydric alcohol containing at least 4 carbon atoms and at least three hydroxyl groups, typified by polyallyl sucrose.

In aqueous systems where a relatively constant viscosity is to be maintained as the amount of an inorganic salt added to the system is increased from about 0.05 to about 3.0 percent by weight, the presence of a crosslinking monomer is generally beneficial. The presence of the crosslinking material in these solutions maintains the texture of the solution. This is particularly important in pharmaceutical and cosmetic applications. Some thickened aqueous solutions are stringy in nature, appearance and feel. This texture may change to a more desirable buttery or smooth consistency as salt is added. The smooth texture can be usually achieved initially and can be easily maintained upon the addition of salt if a crosslinking monomer is present.

Crosslinking monomers in the thickening compositions of this invention are not needed nor preferred if the neutralized copolymer is to be used to thicken an aqueous system which initially contains salt ions (the salt being present at a level of 0.5 to 5 percent by weight in the solution). The brines encountered in oil well drilling are instances of this situation.

Many of the compositions of this invention are superior to gum tragacanth, gum Karaya and other naturally occurring more or less insoluble gum-like substances conventionally used as bodying and suspending agents. The high swelling polymers of this invention are useful in preparing various mucilaginous or colloidal gel-like materials such as dentrifices, surgical jellies, creams and ointments, and printing paste thickeners. They show promise as foam builders and foam stabilizers and as emulsifying agents for water-solvent combination compositions. They also find use in low concentrations by weight as treatment agents for waste water, cooling water and boiler water. In liquid detergent solutions the copolymers serve as clarifying or solubilizing agents as well as thickeners.

Production of the polymers of this invention employs a monomeric mixture which contains two essential monomeric ingredients, each in certain proportions, one being a monomeric olefinically-unsaturated carboxylic acid and the other being an acrylic ester having a long chain aliphatic group. Optionally, there is included in the monomeric mixture a crosslinking monomer, for example, allyl sucrose.

The carboxylic monomers useful in the production of the polymers of this invention are the olefinically-unsaturated carboxylic acids containing at least one activated carbon-to-carbon olefinic double bond, and at least one carboxyl group, that is, an acid containing an olefinic double bond which readily functions in polymerization because of its presence in the monomer molecule either in the alpha-beta position with respect to a carboxyl group thusly,

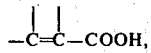

or as a part of a terminal methylene grouping thusly, $CH_2=C<$. In the alpha-beta acids the close proximity of the strongly polar carboxyl group to the double-bonded carbon atoms has a strong activating influence rendering the substances containing this structure very readily polymerizable. The presence of a terminal methylene grouping in a carboxylic monomer makes this type of compound much more easily polymerizable than if the double bond were intermediate in the carbon structure. Olefinically-unsaturated acids of this class include such widely divergent materials as the acrylic acids typified by acrylic acid itself, methacrylic acid, ethacrylic acid, alpha-chloroacrylic acid, alpha-cyano acrylic acid, beta methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same polycarboxylic acid molecule. Anhydrides of the types formed by elimination of water from two or more molecules of the same or different unsaturated acids, such as acrylic anhydride, are not included because of the strong tendency of their polymers to hydrolyze in water and alkali. Maleic anhydride and the other acid anhydrides useful herein have the general structure

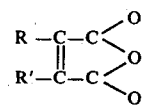

wherein R and R' are selected from the group consisting of hydrogen, halogen, cyanogen (—C ≡ N), hydroxyl, lactam and lactone groups and alkyl, aryl, alkaryl, aralkyl, and cycloalkyl groups such as methyl, ethyl, propyl, octyl, decyl, phenyl, tolyl, xylyl, benzyl, cyclohexyl and the like.

The preferred carboxylic monomers for use in this invention are the monoolefinic acrylic acids having the general structure

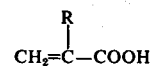

wherein R is a substituent selected from the class consisting of hydrogen, halogen, hydroxyl, lactone, lactam and the cyanogen (—C N) groups, monovalent alkyl radicals, monovalent aryl radicals, monovalent aralkyl radicals, monovalent alkaryl radicals and monovalent cycloaliphatic radicals. Of this class, acrylic acid itself is most preferred because of its generally lower cost, ready availability, and ability to form superior polymers. Another particularly preferred carboxylic monomer is maleic anhydride.

The preferred acrylic ester monomers having long chain aliphatic groups are derivatives of acrylic acid represented by the formula:

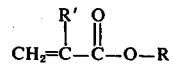

wherein R is a member of the class consisting of alkyl groups having from 8 to 30 carbon atoms, preferably 10 to 22 carbon atoms and R' is hydrogen or a methyl group. Representative higher alkyl acrylic esters are decyl acrylate, lauryl acrylate, stearyl acrylate, behenyl acrylate and melissyl acrylate and the corresponding methacrylates. Mixtures of two or three or more long chain acrylic esters may be successfully polymerized with one of the carboxylic monomers to provide useful thickening resins of this invention.

The preferred crosslinking monomer, if one is employed, is a polyalkenyl polyether having more than one alkenyl ether grouping per molecule. The most useful possess alkenyl groups in which an olefinic double bond is present attached to a terminal methylene grouping, $CH_2=C<$. They are made by the etherification of a polyhydric alcohol containing at least 4 carbon atoms and at least 3 hydroxyl groups. Compounds of this class may be produced by reacting an alkenyl halide, such as allyl chloride or allyl bromide with a strongly alkaline aqueous solution of one or more polyhydric alcohols. The product is a complex mixture of polyethers with varying numbers of ether groups. Analysis reveals only the average number of ether groupings on each molecule. Efficiency of the polyether crosslinking agent increases with the number of potentially polymerizable groups on the molecule. It is preferred to utilize polyethers containing an average of two or more alkenyl ether groupings per molecule. Other crosslinking monomers include for example, diallyl esters, dimethallyl ethers, allyl or methally acrylates and acrylamides, tetraallyl tin, tetravinyl silane, polyalkenyl methanes, diacrylates and dimethacrylates, divinyl compounds, polyallyl phosphate, diallyloxy compounds and phosphite esters and the like.

Monomeric mixtures of the carboxylic monomer and the long chain acrylic ester monomer preferably contain 95 to 50 weight percent carboxylic monomer and 5 to 50 weight percent acrylic ester monomer.

When the optional crosslinking agent is present, polymeric mixtures containing about 0.1% to about 4% by weight of crosslinking monomer based on the total of carboxylic acid monomer plus the long chain alkyl acrylate ester monomer, preferably 0.2 to 1.0% by weight based on the total mixture are employed. Polymers containing less than 5 to 10% by weight of water extractable material are produced with as little as 0.2 to 0.5% by weight of the crosslinker. When 0.1 to 4.0% more preferably 0.20 to 1.0% by weight of the crosslinking monomer is utilized, water-insoluble polymers are obtained, especially with acrylic acids, which are extremely water-sensitive, especially in the form of their monovalent salts, and swell greatly with the absorption of hundreds of times their own weight of water when neutralized with base. When 0.1 to 6.0%, more preferably 0.20 to 2.5% of the crosslinking monomer is copolymerized with maleic anhydride, high-swelling polymers also are obtained. In these interpolymers, the carboxylic monomer or monomers should not be less than 50% of the total monomeric mixture. Three component interpolymers may be made from monomeric mixtures comprising from 60 to 95% of a carboxylic monomer such as acrylic acid, from 39.9 to 4% by weight of a long chain acrylic ester such as lauryl acrylate and from 0.1 to 6% of crosslinking monomer such as polyallyl sucrose, the total parts by weight being equal to 100.

Preferred for use as crosslinked water-swellable artificial gums are tripolymers resulting from the polymerization of monomeric mixtures containing, respectively, from 70 to 95% by weight of acrylic acid, 4 to 29.5% of a second monomer such as lauryl acrylate or stearyl acrylate and 0.5% to 1.0% by weight of a crosslinker such as a polyallyl polyether. It is to be understood that in the above proportions, if a maximum amount of two of the monomers are utilized that somewhat less than maximum amount of the third monomer must be utilized.

The polymers of this invention are preferably made by polymerization in an inert diluent having some solubilizing action on one or more of the monomeric ingredients but substantially none on the resultant polymer. Polymerization in mass may be employed but is not preferred because of the difficulty in working up the solid polymeric masses obtained. Polymerization in an aqueous medium containing a water-soluble free radical catalyst peroxygen is useful, the product being obtained either as a granular precipitate or as a highly swollen gel, either of which may be used directly or are easily further sub-divided and dried. Polymerization in an organic liquid which is a solvent for the monomers but a non-solvent for the polymer, or in a mixture of such solvents, in the presence of a solvent-soluble catalyst is most preferred because the product is usually obtained as a very fine friable and often fluffy precipitate which, after solvent removal, seldom requires grinding or other treatment before use. Suitable solvents for the latter method include benzene, xylene, tetralin, hexane, heptane, carbon tetrachloride, methyl chloride, ethyl chloride, bromo trichloro methane, dimethyl carbonate, diethyl carbonate, ethylene dichloride, and mixtures of these and other solvents.

In accordance with this invention the polymerization is conducted in the presence of a haloethane or methane, preferably containing at least four halogen atoms. Representative materials include for example, a fluoroethane, fluoromethane, chlorofluoromethane, bromofluoroethane, or preferably a chlorofluoroethane or chlorofluoromethane containing at least four halogen atoms including, for example, 1,1,2-trichloro-1,2,2-trifluoroethane, trichlorofluoromethane, tetrafluoromethane, chlorotrifluoromethane, bromotrifluoromethane, 1-chloro-1,1,2,2,2-pentafluoroethane, dichlorodifluoromethane, 1,2-difluoro-1,1,2,2-tetrachloroethane and the like. The amounts of these materials used may be varied from the amount just sufficient to make a slurry of the reactants up to where there is a substantial excess of the chlorofluoroethane, as will be apparent to those skilled in the art. Preferred diluents are those which are solvents for the monomers but non-solvents for the polymers.

Polymerization in the diluent medium is carried out in the presence of a free radical catalyst in a closed vessel in an inert atmosphere and under autogenous pressure or artificially-induced pressure or in an open vessel under reflux at atmospheric pressure. Temperature of the polymerization may be varied from 0° to 100°C., depending to a large degree on the molecular weight desired in the polymer. Polymerization under reflux at 50° to 90°C. under atmospheric pressure using a free radical catalyst is generally effective in bringing a polymer yield of 75% to 100% in less than 10 hours. Suitable catalysts include peroxygen compounds such as sodium, potassium and ammonium persulfates, caprylyl peroxide, benzoyl peroxide, hydrogen peroxide, pelargonyl peroxide, cumene hydroperoxides, tertiary butyl diperphthalate, tertiary butyl perbenzoate, sodium peracetate, sodium percarbonate, and the like as well as azo diisobutyryl nitrile, hereinafter referred to as azoisobutyronitrile. Other catalysts utilizable are the so-called "redox" type of catalyst and the heavy-metal activated catalyst systems. These polymers generally do not attain their maximum properties in water until converted to a partial alkali, ammonium or amine salt. The neutralizing agent is preferably a monovalent alkali such as sodium, potassium lithium or ammonium hydroxide or the carbonates and bicarbonates thereof, or mixtures of the same, and also amine bases having not more than one primary or secondary amino group. Polyvalent bases such as calcium hydroxide usually have a deswelling action on the water-swollen polymers and their salts, although their absolute swell notwithstanding the presence of these polyvalent metal ions is higher than that of the naturally-occurring gum-like materials such as gum tragacanth and the like in the presence of the same deswelling agents.

Copolymers are evaluated as thickeners or viscosity improvers by mixing the copolymer with a base (typically-triethylamine). The neutralized copolymer is dissolved in water. Solution viscosities are then measured with an RVT model Brookfield viscometer. The influence of salts, such as sodium chloride, upon the viscosities of these solutions is observed by measuring viscosity upon the addition of incremental amounts of salt to the solutions.

The invention will now be more fully described in the following specific examples, which are intended as being illustrative only, of the preparation of several types of polymers using various proportions of monomers, polymerization media, temperature, etc. and the effects of these polymers upon the viscosities of aqueous solutions.

EXAMPLE I

A series of batch polymerizations of acrylic acid and stearyl acrylate was carried out in benzene at 65°C. using caprylyl peroxide as the initiator. The reactions were conducted in 12 oz. crown capped glass bottles under dry nitrogen. The polymers, insoluble in benzene, were separated by centrifuging and dried in a vacuum oven at 55°C.

Weight percent stearyl acrylate content of the copolymers and appearance of solutions of 0.5 gram copolymer, 1 ml. of triethylamine and 100 ml. distilled water were as follows:

The data show that copolymer solution viscosity increases through a maximum as the stearyl acrylate content of copolymer increases. Response of the solutions with respect to viscosity loss or increase as salt is added depends on the stearyl acrylate content of the copolymer used. The control water thickener of the prior art exhibits an initial greater viscosity in solution, but this viscosity falls drastically as increments of salt are added.

A control solution with only 0.2 part salt present exhibits totally unsatisfactory viscosity of 2,950 cps while copolymers of the invention maintain viscosities up to 14,500 cps with the same level of salt present. Some of the solutions which are stringy in nature before the addition of salt become more jelly-like or buttery in nature as increasing amounts of salt are added. This change indicates that the salt can be used in conjunction with the polymers of the invention to not only control the solution viscosity as such, but also to control the consistency of the aqueous system.

EXAMPLE II

Employing the procedure of Example I, a series of acrylic acid-stearyl methacrylate copolymers was made and evaluated with results shown in Table 2.

TABLE II

| Polymer | Weight % Stearyl Methacrylate | Appearance of solution no salt added | Brookfield viscosity - cps Salt added - grams | | | | |
|---------|---|---|---|---|---|---|---|
| | | | None | 0.05 | 0.1 | 0.2 | 0.3 |
| A | 4.4 | clear, stringy | 200 | — | — | — | — |
| B | 12.0 | clear, very stringy | 5600 | 3700 | 3350 | 7500 | 12300 |
| C | 18.5 | clear, very stringy, slightly grainy | 8500 | 7100 | 9400 | 17900 | 16050 |
| D | 26.7 | clear, stringy, somewhat grainy | 3150 | 6250 | 7450 | 11250 | 8850 |
| E | 33.4 | clear, grainy, not so stringy, more buttery | 1400 | 2150 | 3700 | 4250 | 3500 |
| Control* | | | 42280 | 18500 | 9250 | 2450 | 1400 |

*Copolymer of acrylic acid (98.5 weight percent) and allyl sucrose (1.5 weight percent) swelling index 600

The data show that solution viscosity rises to a maximum, then falls off as the weight percent stearyl methacrylate increases. Resistance to viscosity drop as the amount of salt is increased also rises to a maximum and then declines as weight percent stearyl methacrylate increases. Optimum weight percent stearyl methacrylate is determined by the concentration of the salt solutions that are to be thickened.

Again, the control solutions have fallen to unsatisfactory levels of viscosity (below about 3,000 cps.) when 0.2 part of salt is added. Similar solutions of the invention show viscosities up to 17,900 cps.

The neutralized acrylic acid-stearyl methacrylate copolymers form very viscous solutions even when

TABLE I

| Polymer | Weight % Stearyl Acrylate | Appearance of Solution no salt added | Brookfield Viscosity - cps Salt added - grams | | | | |
|---------|---|---|---|---|---|---|---|
| | | | None | 0.05 | 0.1 | 0.2 | 0.3 |
| A | 8.3 | smooth, clear | 100 | — | — | — | — |
| B | 11.6 | slightly hazy, very stringy | 1550 | 850 | 800 | 1750 | 2650 |
| C | 15.1 | slightly hazy, very stringy | 5750 | 3800 | 5750 | 9350 | 8800 |
| D | 21.9 | hazy, very stringy, slightly grainy | 7800 | 10450 | 12150 | 13500 | 12050 |
| E | 24.1 | hazy, cloudy, very stringy, somewhat grainy | 7700 | 12800 | 13000 | 14500 | 10250 |
| F | 25.8 | cloudy, stringy, grainy | 7650 | 10900 | 11950 | 8950 | 5450 |
| Control* | | | 42250 | 18500 | 9250 | 2950 | 1400 |

*Copolymer of acrylic acid (98.5 weight percent) and allyl sucrose (1.5 weight percent) swelling index 600.

present at low concentration by weight.

It is unexpected to find solutions of this type that increase in viscosity as sodium chloride is added.

Similar results were obtained when a series of copolymers and test solutions were made as in Example I, except that lauryl acrylate was used as a replacement for stearyl acrylate.

EXAMPLE III

Employing the procedure of Example I, two series of acrylic acid-stearyl methacrylate - polyallyl sucrose terpolymers was made and evaluated with results shown in Table 3. The test solutions comprised 1 gram of polymer, 2 ml. triethylamine and 100 ml. water. The first series of terpolymer contained 0.5 weight percent crosslinker. The second series contained 1.0 weight percent crosslinker.

TABLE III

| Polymer | Weight Percent Acrylic Acid | Weight Percent Stearyl Methacrylate | Weight Percent Polyallyl Sucrose | Brookfield Viscosity - cps Salt added - grams | | | | | |
|---|---|---|---|---|---|---|---|---|---|
| | | | | None | 0.2 | 0.4 | 0.6 | 0.8 | 2.0 |
| A | 94.56 | 4.94 | 0.5 | 22.400 | 14550 | 13150 | 15100 | 16400 | 12350 |
| B | 89.62 | 9.88 | 0.5 | 32900 | 30350 | 32900 | 36250 | 31500 | 6700 |
| C | 84.67 | 14.83 | 0.5 | 43650 | 41200 | 43000 | 38400 | 30600 | 1750 |
| D | 79.75 | 19.75 | 0.5 | 52500 | 47450 | 40750 | 23800 | 15050 | <600 |
| E | 99.5 | 0 | 0.5 | 20500 | 9800 | 7300 | 5350 | 4250 | 1800 |

E is a prior art control thickener

TABLE IV

| F | 93.95 | 5.05 | 1.0 | 61800 | 33850 | 27400 | 22650 | 14700 | 6650 |
|---|---|---|---|---|---|---|---|---|---|
| G | 91.25 | 9.75 | 1.0 | 61000 | 45450 | 39400 | 30250 | 21500 | 2850 |
| H | 84.38 | 14.62 | 1.0 | 56600 | 57400 | 42900 | 25750 | 18350 | 1050 |
| I | 79.5 | 19.50 | 1.0 | 71200 | 50400 | 30700 | 15950 | 8000 | <600 |
| J | 99 | 0 | 1.0 | 32850 | 18000 | 13100 | 10150 | 8300 | 3250 |

J is a prior art control thickener

Cross-linked terpolymers show higher salt containing solution viscosities than do such solutions containing control thickeners of crosslinked carboxylic acid. Terpolymers containing 1% crosslinker provide solutions with higher viscosities than equivalent solutions containing only 0.5% cross-linker in the thickener.

Solutions exhibit higher viscosities as the weight percent alkyl acrylate ester present is increased.

Response of the solution or mucilage produced with respect to viscosity increase or loss as salt is added in increasing amounts depends upon the long chain acrylate ester content of the terpolymer and also upon the crosslinker content of the terpolymer.

EXAMPLE IV

Following the procedure of Example I a series of polymerizations was run wherein 95 mol percent of acrylic acid was copolymerized with 5 mol percent of a number of long chain alkyl acrylate esters wherein the chain length of the alkyl ester ranged from 8 carbon atoms (exemplary of the prior art) to 18 carbon atoms. Solutions of one gram copolymer, 2 milliliters triethylamine and 100 ml distilled water exhibited viscosities as shown in Table 4.

TABLE 4

| | C Atoms in Alkyl Ester | Viscosity |
|---|---|---|
| A | 18 - octadecyl | 45000 |
| B | 16 - hexadecyl | 26000 |
| C | 12 - dodecyl | 4500 |
| D | 10 - decyl | 1000 |
| E | 8 - octyl | 350 |

TABLE 4-continued

| | C Atoms in Alkyl Ester | Viscosity |
|---|---|---|
| F | 6 - hexyl | 250 |

Increasing length of the alkyl ester chain leads to increasing viscosities. An unexpected sharp break point in viscosity increase occurs between chains of 8 and 10 carbon atoms.

EXAMPLE V

Two polymerizations were conducted to compare the results obtained using benzene and 1,1,2-trichloro-1,2,2-trifluoroethane. In one procedure, following the general process of Example I, 10.8 grams of lauryl methacrylate, 16.2 grams acrylic acid and 1.3 ml caprylyl peroxide solution of 1.375 grams peroxide in 125 ml. benzene solvent were dissolved in 200 milliliters (185.99 grams) of benzene. In another procedure, 32.4 grams of lauryl methacrylate, 48.6 grams acrylic acid and 13 ml. caprylyl peroxide solution (4.14 grams peroxide in 125 ml. 1,1,2-trichloro-1,2,2-trifluoroethane) were dissolved in 600 ml. (938 grams) of 1,1,2-trichloro-1,2,2-trifluoroethane. The polymerization reactions were conducted at 65°C. for 16 hours. In both cases the polymers were separated from the carrier by centrifuge. It was observed that discrete particles of the polymer prepared in the chlorofluoroethane were readily separated while there was more difficulty in separating the swollen particles from the benzene polymerization. The improvement in water thickening efficiency of the copolymers prepared in chlorofluoroethane is shown in the following data.

| | 40/60 LM-AA copolymer made in benzene at 65°C. | 40/60 LM-AA copolymer made in Freon 113 at 65°C. |
|---|---|---|
| Brookfield viscosity (RVT, 20 rpm, No. 6) in cps. of a 1% solution of triethylamine neutralized copolymer | 3,400 | 15,100 |
| Brookfield viscosity (RVT, 20 rpm, No. 6) in cps. of a 0.5% solution of triethylamine neutralized copolymer | 200 | 6,950 |
| Brookfield viscosity (RVT, 20 rpm, No. 4) in cps. of a 0.2% solu- | | |

| | 40/60 LM-AA copolymer made in benzene at 65°C. | 40/60 LM-AA copolymer made in Freon 113 at 65°C. |
|---|---|---|
| tion of triethylamine neutralized copolymer | very low | 5,150 |

The procedure using the 1,1,2-trichloro-1,2,2-trifluoroethane was repeated with comonomers in proportions of dodecyl methacrylate/acrylic acid of 10/90, 15/85, 20/80 and 30/70 in both benzene and the chlorofluoroethane. In all cases the chlorofluoroethane solution prepared copolymers had superior water thickening efficiencies as compared to those prepared in benzene, and the thickening efficiencies of copolymers at low concentrations, 0.2 to 0.5% are substantially higher for the polymers prepared in the chlorofluoroethane.

The effect of sodium chloride on the Brookfield viscosity of 1% aqueous mucilage in the lauryl methacrylate series is demonstrated below.

| Gms. NaCl | 10/90 | 15/85 | 20/80 | 30/70 | 30/70 |
|---|---|---|---|---|---|
| 0.00 | 10,900 | 11,100 | 17,488 | 13,000 | 15,800 |
| 0.10 | — | — | 30,250 | 15,200 | 16,380 |
| 0.25 | 8,700 | 26,250 | 44,600 | 11,300 | 10,500 |
| 0.50 | 13,300 | 48,900 | 53,000 | 8,850 | 1,360 |
| 0.75 | — | 82,800 | 73,200 | 7,300 | 75 |
| 1.00 | 26,650 | 80,150 | 54,200 | 4,000 | 70 |
| 1.50 | 58,600 | 73,000 | 28,600 | — | phase separation |
| 2.00 | 65,100 | — | 14,800 | — | phase separation |
| 3.00 | — | — | 2,150 | — | phase separation |
| 4.00 | — | — | 1,000 | — | phase separation |

The copolymers in the dodecyl methacrylate series show higher efficiencies as water thickeners. Excellent optimum efficiency occurs at lauryl methacrylate contents between about 20 to 30 weight percent. Within this range the copolymers made with the chlorofluoroethane even in 0.1% aqueous mucilage have viscosities of 2,000 cps.

The Example was repeated to prepare copolymers containing 5 and 45 weight percent octadecyl methacrylate to polymerization conversions of 90 and 97% obtained after 2 to 4 hours at 65°C.

I claim:

1. A process for preparing copolymers of unsaturated copolymerizable carboxylic acid monomers and acrylic acid esters of the formula

wherein R contains 10 to 30 carbon atoms and R' is hydrogen or methyl, comprising conducting copolymerization of from 95 to 50 weight percent of said acid monomer and 5 to 50 percent of said ester monomer in the presence of a haloalkane containing 1 to 2 carbon atoms and at least 4 halogen atoms.

2. The process of claim 1 wherein the haloalkane is a chlorofluoroalkane.

3. The process of claim 2 wherein the chlorofluoro alkane contains 2 carbon atoms and 6 halogen atoms.

4. The process of claim 3 wherein said acid monomer is selected from the group consisting of acrylic acid, methacrylic acid, maleic acid, and anhydrides thereof.

5. The process of claim 4 wherein there is copolymerized with said acid monomer and acrylic ester monomer a polymerizable crosslinking monomer containing $CH_2=C<$ groups and at least one other polymerizable grouping, the unsaturated bonds of said polymerizable grouping being non-conjugated with respect to the other.

6. A process of claim 5 wherein said chlorofluoroethane is 1,1,2-trichloro-1,2,2-trifluoroethane.

7. A process of claim 6 wherein in the acrylic ester monomer R is lauryl or stearyl and R' is hydrogen or methyl.

8. A process of claim 7 wherein said polymer contains a crosslinking monomer comprising a polyalkenyl polyether of a polyhydric alcohol containing more than one alkenyl group per molecule wherein the polyhydric alcohol contains at least 4 carbon atoms and at least three hydroxyl groups.

9. A process of claim 8 wherein said crosslinking monomer is a monomeric polyether of an oligosaccharide and hydroxyls are etherified with allyl groups.

10. A process of claim 9 wherein said carboxylic acid monomer and acrylic ester monomer are dissolved in said chlorofluoroethane.

* * * * *